(12) United States Patent
Gaetani et al.

(10) Patent No.: US 8,758,835 B2
(45) Date of Patent: Jun. 24, 2014

(54) COMPOSITION USEFUL FOR THE PREVENTION OR REDUCTION OF THE PROGRESSION OF PROSTATE CANCER

(75) Inventors: Franco Gaetani, Ariccia (IT); Ashraf Virmani, Ariccia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 277 days.

(21) Appl. No.: 13/001,661

(22) PCT Filed: Jul. 24, 2009

(86) PCT No.: PCT/EP2009/059531
§ 371 (c)(1),
(2), (4) Date: Feb. 28, 2011

(87) PCT Pub. No.: WO2010/012651
PCT Pub. Date: Feb. 4, 2010

(65) Prior Publication Data
US 2011/0262417 A1    Oct. 27, 2011

(30) Foreign Application Priority Data
Jul. 31, 2008   (EP) .................................... 08161516

(51) Int. Cl.
*A61K 36/80* (2006.01)
*A61K 36/00* (2006.01)

(52) U.S. Cl.
USPC ........... 424/729; 424/725; 424/777; 424/641; 424/702

(58) Field of Classification Search
None
See application file for complete search history.

(56) References Cited

U.S. PATENT DOCUMENTS

| | | | |
|---|---|---|---|
| 6,030,622 A * | 2/2000 | Shehadeh | 424/729 |
| 6,572,899 B1 | 6/2003 | Gorsek | |
| 6,599,540 B1 * | 7/2003 | Fabre et al. | 424/727 |
| 6,818,234 B1 * | 11/2004 | Nair et al. | 424/777 |
| 2005/0049424 A1 * | 3/2005 | Kelly et al. | 549/234 |
| 2005/0100622 A1 * | 5/2005 | Nair et al. | 424/777 |
| 2005/0261367 A1 * | 11/2005 | Murad | 514/492 |
| 2006/0216251 A1 * | 9/2006 | Morariu | 424/59 |
| 2006/0251750 A1 * | 11/2006 | Tabor | 424/757 |
| 2007/0041994 A1 * | 2/2007 | McDowell, Jr. | 424/195.15 |
| 2008/0038369 A1 * | 2/2008 | Clark | 424/643 |

FOREIGN PATENT DOCUMENTS

| | | |
|---|---|---|
| DE | 200 09 840 | 8/2000 |
| DE | 20009840 U1 * | 8/2000 |
| DE | 20 2005 020103 | 4/2006 |
| DE | 202005020103 U1 * | 6/2006 |
| WO | 99/66941 | 12/1999 |
| WO | 00/57892 | 10/2000 |
| WO | 03/035635 | 5/2003 |
| WO | 03/086442 | 10/2003 |
| WO | 2008/051586 | 5/2008 |

OTHER PUBLICATIONS

Schmidt et al., "A natural history of botanical therapeutics" Metabolism: Clinical and Experimental, vol. 57, No. 7, Jul. 2008, pp. S3-S9.
Syed et al., "Dietary agents for chemoprevention of prostate cancer" Cancer Letters, vol. 265, No. 2, Jul. 2008, pp. 167-176.
Siddiqui et al., "Prevention of prostate cancer through custom tailoring of chemopreventive regimen" Chemico-Biological Interactions, vol. 171, No. 2, Jan. 2008, pp. 122-132.

* cited by examiner

*Primary Examiner* — Chris R Tate
(74) *Attorney, Agent, or Firm* — Lucas & Mercanti, LLP

(57) ABSTRACT

It is described a composition comprising as active ingredients green tea extract and pomegranate extract for the prevention or reduction of the progression of prostate cancer.

7 Claims, No Drawings

COMPOSITION USEFUL FOR THE PREVENTION OR REDUCTION OF THE PROGRESSION OF PROSTATE CANCER

CROSS-REFERENCE TO RELATED APPLICATIONS

This application is 371of PCT/EP2009/059531 filed on Jul. 24, 2009, which claims the benefit of European Patent Application No. 08161516.3 filed on Jul. 31, 2008, the contents of each of which are incorporated herein by reference.

The present invention relates to a composition useful for the prevention or reduction of the progression of prostate cancer.

In particular, the present invention relates to a composition, which comprises as active ingredients green tea and pomegranate extract, useful for the prevention or reduction of the progression of prostate cancer.

Prostate cancer is the most common cancer in mammals, especially among human males in the western countries (Cancer Statistics 1997, CA Cancer J. Clin. 1997; 47; 5-27).

Various factors such as an unknown aetiology, variable pathology, an intricate relationship to endocrine factors, and anaplastic progression contribute to the complexity of this disease.

A team of researchers from the University of Wisconsin, Madison, Wis., and Case Western Reserve University, Cleveland, Ohio, documented the role of green tea polyphenols (GTP) in modulating the insulin-like growth factor-1 (IGF-1)-driven molecular pathway in prostate tumor cells in a mouse model for human prostate cancer. These observations bear significance in light of studies that indicate how increased levels of IGF-1 are associated with increased risk of several cancers, such as prostate, breast, lung and colon. The green tea polyphenols contributed to minimizing tumor development by governing the amount of vascular endothelial growth factor (VEGF) in the serum of the prostate cancer mouse model. The reduction of VEGF may result from GTP-induced suppression of IGF-1 levels. VEGF functions to recruit and develop new blood vessels that carry nutrients to developing tumors. By reducing the amount of VEGF, GTP works to minimize nutrients flowing to and supporting tumor growth.

In Clinical Cancer Research, Jul. 1, 2006; pp 4018-4026 and Clinical Cancer Research Vol. 12, 4018-4026, Jul. 1, 2006, is reported that pomegranate extract may be useful for the prevention or reduction of the progression of prostate cancer.

In Prostate Cancer and Prostatic Diseases (2002) 5, 6-12 is reported that lycopene may be useful for the prevention or reduction of the progression of prostate cancer.

In WO0057892 is reported that serenoa is useful for the treatment of prostate cancer.

In WO 03035635 is reported that isoflavonoid derivatives are useful for the treatment of prostate cancer;

In WO04091602 is reported that L-carnitine is useful the treatment of cardiovascular diseases.

Selenium in humans is a trace element nutrient which functions as cofactor for reduction of antioxidant enzymes such as glutathione peroxidases. Dietary selenium comes from nuts, cereals, meat, fish and eggs. The "Nutritional Prevention of Cancer Project" (NPC) was a controlled, randomized cancer prevention trial in which 1,312 patients received a daily 200 µg dose of selenium or a placebo for up to 10 years. In this study a statistically significant reduction in the incidence of prostate cancer and prostate cancer progression was obtained.

Although the anti-carcinogenic effects of green tea and pomegranate extract have already been known, none of the prior art documents cited above mention nor suggest the use of these two active ingredients in combination for the prevention or reduction of the progression of prostate cancer.

Furthermore, while there are other agents available for chemotherapy of tumors, and other invasive treatment options exist for prostate cancer such as removal of the cancerous prostate or placement of a radioactive seed designed to shrink the tumor, it would be more desirable to provide a composition useful as an adjunct or complement to traditional therapies of low toxicity to a patient which will serve as an anti-carcinogenic agent for prostate cancer.

It is therefore one object of the present invention a synergistic composition comprising as active ingredients green tea extract and pomegranate extract.

The composition mentioned above may further comprise lycopene, selenium, zinc, serenoa, isoflavonoid derivatives and L-carnitine.

It is a further object of the present invention a composition comprising:

(a) green tea extract, as active ingredient, in a dose of from 25 to 800 mg, preferred doses are 125 and 250 mg; and
(b) pomegranate extract, as active ingredient, in a dose of from 25 to 800 mg, the preferred doses are 40, 125 and 250 mg; and
(c) lycopene in a dose of from 0.03 to 30.0 mg, the preferred dose are 1.25 and 5 mg;
(d) selenium in a dose of from 8.2 to 500 µg, the preferred doses are 55 and 82.5 µg,
(d) zinc in a dose of from 1 to 200 mg, the preferred dose is 20 mg; and
(e) serenoa in a dose of from 10 to 400 mg, the preferred doses are 160 and 320 mg;
(f) isoflavonoid derivatives (soya isoflavon) in a dose of from 10 to 500 mg, the preferred dose is 100 mg; and
(g) L-carnitine in a dose of from 50 to 500 mg, the preferred dose is 200 mg.

It is a further object of the present invention the use of the composition mentioned above, for the prevention or reduction of the progression of prostate cancer.

It is a further object of the present invention the use of the composition mentioned above, for preparing a medicament for the prevention or reduction of the progression of prostate cancer.

It is a further object of the present invention the use of the composition mentioned above, for preparing a dietary supplement for the prevention or reduction of the progression of prostate cancer.

The composition of the invention may further comprise co-enzymes, mineral substances, antioxidants, vitamins and agents useful for treating prostate cancer.

The following non limiting examples further illustrate the invention.

EXAMPLE 1

For the experiments reported in the following established human prostate carcinoma cell lines LNCaP and PC3 (obtained from the American Type Culture Collection Rockville, Md.) were used.

The LNCaP cells were cultured in RPMI 1640 medium (Life Technologies, Rockville, Md.), supplemented with 10% Fetal Bovine Serum (FBS) and 1% Penicillin and Streptomycin. The cells were incubated at 37 degree C. in a humidified atmosphere of 5% CO2 in air. Both sets of cell cultures were grown to 80% confluence in 10 cm tissue culture flasks and split 1:8. The cells were plated in 96 cell plates and allowed to attach and reach 60-70% confluence before being used for experimentation.

Effect on Cell Growth in Vitro

The cultured set of LNCaP and PC3 cells were treated with either green tea extract (40 µg/ml in PBS), pomegranate extract (40 µg/ml in PBS) or in combination (both green tea extract and pomegranate extract) in 10 wells each containing complete cell medium. Cells that were used as control were incubated with same amount of PBS in complete cell medium. The effects of lycopene (5 mmol/L], selenium (30 ng/ml), zinc (10 µg/ml), serenoa (10 µg/ml), and soya isoflavon (10 µg/ml) were also tested by adding them to the cell culture alone or in combination with the green tea extract and pomegranate extract. The cellular proliferation of the cells was determined using the 3-(4,5-dimethylthiazol-2-yl)-2,5-diphenyltetrazolium (MTT) colorimetric assay following 24 hours of incubation at 37° C. with or without the test agents. The MTT (5 ng/ml) was added to all the wells and incubated for a further 2 hr. The plate was than centrifuged at 500×g for 5 min at 4 degree C. The MTT solution was removed from the wells by careful aspiration and buffered DMSO (0.1 ml) was added to each of the wells and plates shaken for 15 mins. The absorbance was measured on a microplate reader at the wavelength of 540 nm. The effect of each compound alone and in combination on cell growth was assessed as the percentage of cell viability in which the untreated control cells were taken as those being completely viable and allowed to grow freely.

The results obtained are reported in the following Tables 1-4.

TABLE 1

Effects of test compounds on LNCaP cell proliferation

| N° | Control | A | B | C | D | E | A + B | A + B + C + D + E |
|---|---|---|---|---|---|---|---|---|
| 1 | 346 | 319 | 349 | 353 | 328 | 316 | 298 | 266 |
| 2 | 345 | 320 | 344 | 341 | 322 | 334 | 272 | 245 |
| 3 | 311 | 324 | 313 | 301 | 303 | 332 | 283 | 287 |
| 4 | 358 | 365 | 322 | 312 | 302 | 308 | 286 | 255 |
| 5 | 364 | 303 | 308 | 317 | 309 | 342 | 247 | 243 |
| 6 | 350 | 322 | 302 | 301 | 323 | 324 | 263 | 277 |
| 7 | 334 | 315 | 289 | 344 | 297 | 311 | 286 | 273 |
| 8 | 367 | 322 | 324 | 329 | 301 | 313 | 259 | 271 |
| 9 | 342 | 291 | 299 | 315 | 322 | 325 | 282 | 314 |
| 10 | 344 | 323 | 311 | 327 | 307 | 344 | 256 | 311 |
| Mean | 346 | 320 | 316 | 324 | 311 | 325 | 273 | 274 |
| SE | 5 | 6 | 6 | 6 | 4 | 4 | 5 | 8 |
| P< vs control | | 0.01 | 0.01 | 0.05 | 0.001 | 0.01 | 0.001 | 0.001 |
| P< vs A | | | | | | | 0.001 | 0.001 |
| P< vs B | | | | | | | 0.001 | 0.001 |
| P< vs C | | | | | | | 0.001 | 0.001 |
| P< vs D | | | | | | | 0.001 | 0.001 |
| P< vs E | | | | | | | 0.001 | 0.001 |
| % inhib | | 7.5 | 8.7 | 6.4 | 9.8 | 5.7 | 20.9 | 20.5 |

A = green tea extract; B = pomegranate extract; C = lycopene; D = selenium; E = zinc.

TABLE 2

Effects of test compounds on PC3 cell proliferation

| N° | Control | A | B | C | D | E | A + B | A + B + C + D + E |
|---|---|---|---|---|---|---|---|---|
| 1 | 394 | 329 | 319 | 316 | 313 | 321 | 258 | 305 |
| 2 | 366 | 345 | 322 | 382 | 321 | 339 | 260 | 234 |
| 3 | 365 | 301 | 314 | 308 | 374 | 344 | 283 | 224 |
| 4 | 340 | 337 | 377 | 377 | 309 | 355 | 242 | 266 |
| 5 | 371 | 333 | 365 | 314 | 341 | 322 | 248 | 287 |
| 6 | 337 | 324 | 279 | 322 | 345 | 395 | 270 | 263 |
| 7 | 401 | 378 | 281 | 309 | 286 | 344 | 278 | 288 |
| 8 | 388 | 304 | 310 | 299 | 292 | 312 | 261 | 289 |
| Mean | 370 | 331 | 321 | 328 | 323 | 342 | 263 | 270 |
| SE | 8 | 9 | 12 | 11 | 10 | 9 | 5 | 10 |
| P< vs control | | 0.01 | 0.01 | 0.01 | 0.01 | 0.05 | 0.001 | 0.001 |
| P< vs A | | | | | | | 0.001 | 0.001 |
| P< vs B | | | | | | | 0.001 | 0.001 |
| P< vs C | | | | | | | 0.001 | 0.001 |
| P< vs D | | | | | | | 0.001 | 0.001 |
| P< vs E | | | | | | | 0.001 | 0.001 |
| % inhib | | 10.5 | 13.2 | 11.4 | 12.7 | 7.8 | 28.9 | 27.0 |

TABLE 3

Effects of test compounds on LNCaP cell proliferation

| N° | Control | A | B | F | G | H | A + B | A + B + F + G + H |
|---|---|---|---|---|---|---|---|---|
| 1 | 345 | 334 | 352 | 345 | 301 | 345 | 277 | 288 |
| 2 | 365 | 342 | 312 | 351 | 389 | 368 | 289 | 246 |
| 3 | 371 | 311 | 302 | 314 | 311 | 366 | 274 | 299 |
| 4 | 366 | 348 | 343 | 396 | 364 | 354 | 252 | 244 |
| 5 | 326 | 308 | 318 | 304 | 345 | 312 | 265 | 234 |
| 6 | 380 | 313 | 341 | 322 | 328 | 344 | 255 | 291 |
| 7 | 387 | 317 | 288 | 315 | 298 | 325 | 274 | 264 |
| 8 | 352 | 326 | 320 | 333 | 311 | 345 | 261 | 276 |
| 9 | 367 | 298 | 304 | 312 | 301 | 355 | 284 | 311 |
| 10 | 332 | 344 | 342 | 325 | 319 | 352 | 266 | 302 |
| Mean | 359 | 324 | 322 | 332 | 327 | 347 | 270 | 276 |
| SE | 6 | 5 | 7 | 9 | 10 | 5 | 4 | 9 |
| $P<$ vs Control | — | 0.01 | 0.01 | 0.05 | 0.05 | ns | 0.001 | 0.001 |
| $P<$ vs A | | | | | | | 0.001 | 0.001 |
| $P<$ vs B | | | | | | | 0.001 | 0.001 |
| $P<$ vs F | | | | | | | 0.001 | 0.001 |
| $P<$ vs G | | | | | | | 0.001 | 0.001 |
| $P<$ vs H | | | | | | | 0.001 | 0.001 |
| % inhib | | 9.7 | 10.3 | 7.5 | 8.9 | 3.3 | 24.8 | 23.1 |

A = green tea extract; B = pomegranate extract; F = serenoa; G = soya isoflavon; H = L-carnitine

TABLE 4

Effects of test compounds on PC3 cell proliferation
Effects of test compounds on PC3 cell proliferation

| N° | Control | A | B | F | G | H | A + B | A + B + F + G + H |
|---|---|---|---|---|---|---|---|---|
| 1 | 399 | 354 | 324 | 309 | 322 | 392 | 264 | 226 |
| 2 | 373 | 325 | 352 | 386 | 359 | 385 | 254 | 239 |
| 3 | 381 | 331 | 331 | 314 | 345 | 385 | 286 | 241 |
| 4 | 365 | 323 | 381 | 389 | 352 | 366 | 234 | 264 |
| 5 | 384 | 339 | 366 | 312 | 344 | 341 | 261 | 281 |
| 6 | 345 | 368 | 312 | 355 | 385 | 387 | 277 | 261 |
| 7 | 395 | 342 | 265 | 341 | 377 | 320 | 246 | 228 |
| 8 | 388 | 367 | 356 | 332 | 365 | 378 | 251 | 277 |
| Mean | 379 | 344 | 336 | 342 | 356 | 369 | 259 | 252 |
| SE | 6 | 6 | 13 | 11 | 7 | 9 | 6 | 8 |
| $P<$ vs Control | — | 0.01 | 0.01 | 0.01 | 0.05 | ns | 0.001 | 0.001 |
| $P<$ vs A | | | | | | | 0.001 | 0.001 |
| $P<$ vs B | | | | | | | 0.001 | 0.001 |
| $P<$ vs F | | | | | | | 0.001 | 0.001 |
| $P<$ vs G | | | | | | | 0.001 | 0.001 |
| $P<$ vs H | | | | | | | 0.001 | 0.001 |
| % inhib | | 9.2 | 11.3 | 9.8 | 6.1 | 2.6 | 31.7 | 33.5 |

A = green tea extract; B = pomegranate extract; F = serenoa; G = soya isoflavon; H = L-carnitine The results reported in Tables 1, 2, 3 and 4 show that the composition of the invention is statistically more active respect to the single constituents.

Moreover, the presence of lycopene, selenium and zinc, or serenoa, soya isoflavon and L-carnitine did not increase the inhibitory activity of the composition of the invention.

EXAMPLE 2

Experiment 2 Effect on Cell Division in Vitro

The LNCaP and PC3 cells in 25 ml culture flasks were treated either with: green tea extract (40 µg/ml in PBS), pomegranate extract (40 µg/ml in PBS) serenoa (10 µg/ml), soya isoflavon (10 µg/ml) or the combination of green tea extract plus pomegranate extract.

Controls received PBS alone. Treatment was started 48 hrs after attachment. The cells were allowed to grow in culture for up to 72 hrs before being analysed by flow cytometry. The cells were pulse labelled with 10 mM bromodeoxyuridine (BrdU) for 2 hours with or without prior treatment with green tea extract or pomegranate extract or both to asynchronously growing cells. Cells were then harvested, fixed with 70% ethanol, treated with 0.1% HCl and heated for 10 min at 90 degree C. to expose the labelled DNA. Cells were stained with anti-BrdU conjugated FITC (Becton Dickinson) and counterstained with propidium iodide. Cell cycle analysis was carried out on a Becton-Dickinson FACScan, using Lysis II software.

The results of the flow cytometric analysis obtained using the composition of the invention respect to the single components are reported in the following Tables.

TABLE 5

Green Tea Extract,
LNCaP Cell Division BrdU

| Time hr | \multicolumn{4}{c}{Cells Cycle %} |
|---|---|---|---|---|
| | 0 | 24 | 48 | 72 |
| G1 | 73 | 80 | 82 | 77 |
| S | 21 | 18 | 16 | 15 |
| G2/M | 6 | 2 | 2 | 8 |
| % inhibition S phase vs 0 hr | | 14.3 | 23.8 | 28.6 |

TABLE 6

Pomegranate Extract,
LNCaP Cell Division BrdU

| Time hr | Cells Cycle % | | | |
|---|---|---|---|---|
| | 0 | 24 | 48 | 72 |
| G1 | 74 | 69 | 68 | 64 |
| S | 20 | 19 | 16 | 16 |
| G2/M | 6 | 12 | 16 | 20 |
| % inhibition S phase vs 0 hr | | 5.0 | 20.0 | 20.0 |

TABLE 7

Serenoa Extract,
LNCaP Cell Division BrdU

| Time hr | Cells Cycle % | | | |
|---|---|---|---|---|
| | 0 | 24 | 48 | 72 |
| G1 | 70 | 68 | 71 | 62 |
| S | 18 | 18 | 18 | 14 |
| G2/M | 12 | 14 | 11 | 24 |
| % inhibition S phase vs 0 hr | | 0 | 0 | 22.2 |

TABLE 8

Soya isoflavon Extract,
LNCaP Cell Division BrdU

| Time hr | Cells Cycle % | | | |
|---|---|---|---|---|
| | 0 | 24 | 48 | 72 |
| G1 | 72 | 71 | 69 | 63 |
| S | 22 | 21 | 18 | 17 |
| G2/M | 6 | 8 | 13 | 20 |
| % inhibition S phase vs 0 hr | | 4.5 | 18.2 | 22.7 |

TABLE 9

Green Tea plus Pomegranate Extract,
LNCaP Cell Division BrdU

| Time hr | Cells Cycle % | | | |
|---|---|---|---|---|
| | 0 | 24 | 48 | 72 |
| G1 | 72 | 83 | 83 | 79 |
| S | 23 | 11 | 8 | 9 |
| G2/M | 5 | 6 | 9 | 12 |

TABLE 9-continued

Green Tea plus Pomegranate Extract,
LNCaP Cell Division BrdU

| Time hr | Cells Cycle % | | | |
|---|---|---|---|---|
| | 0 | 24 | 48 | 72 |
| % inhibition S phase vs 0 hr | | 52.2 | 65.2 | 60.9 |

TABLE 10

Green Tea Extract PC3
Cell Division BrdU

| Time hr | Cells Cycle % | | | |
|---|---|---|---|---|
| | 0 | 24 | 48 | 72 |
| G1 | 64 | 69 | 65 | 72 |
| S | 30 | 26 | 23 | 22 |
| G2/M | 6 | 5 | 12 | 6 |
| % inhibition S phase vs 0 hr | | 13.3 | 23.3 | 26.7 |

TABLE 11

Pomegranate Extract PC3
Cell Division BrdU

| Time hr | Cells Cycle % | | | |
|---|---|---|---|---|
| | 0 | 24 | 48 | 72 |
| G1 | 66 | 71 | 68 | 69 |
| S | 28 | 25 | 23 | 22 |
| G2/M | 6 | 4 | 9 | 9 |
| % inhibition S phase vs 0 hr | | 10.7 | 17.9 | 21.4 |

TABLE 12

Serenoa Extract PC3
Cell Division BrdU

| Time hr | Cells Cycle % | | | |
|---|---|---|---|---|
| | 0 | 24 | 48 | 72 |
| G1 | 68 | 70 | 69 | 67 |
| S | 29 | 26 | 21 | 20 |
| G2/M | 3 | 4 | 10 | 13 |
| % inhibition S phase vs 0 hr | | 10.3 | 27.6 | 31.0 |

TABLE 13

Soya isoflavon Extract PC3
Cell Division BrdU

| Time hr | Cells Cycle % | | | |
|---|---|---|---|---|
| | 0 | 24 | 48 | 72 |
| G1 | 63 | 68 | 66 | 68 |
| S | 25 | 26 | 23 | 25 |
| G2/M | 12 | 6 | 11 | 7 |
| % inhibition S phase vs 0 hr | | 4.0 | 8.0 | 0 |

TABLE 14

Green Tea plus Pomegranate Extract
PC3 Cell Division BrdU

| Time hr | Cells Cycle % | | | |
|---|---|---|---|---|
| | 0 | 24 | 48 | 72 |
| G1 | 63 | 72 | 78 | 79 |
| S | 31 | 21 | 17 | 14 |
| G2/M | 6 | 7 | 5 | 7 |
| % inhibition S phase vs 0 hr | | 32.3 | 45.2 | 54.8 |

The use of the single compounds shows an inhibitory action on the proliferation of both LNCaP and PC3 cells (see tables 5-8 and 10-13). The results reported in Tables 9 and 14 show that the combination composition of the invention is endowed with an unexpected synergistic effect for the inhibition of the proliferation of both LNCaP and PC3 cells. The cell lines arrest in the S phase persisted for 72 hours by a maximum of 60.9% and 54.8% in LNCaP and PC3 lines, respectively.

No effects on cell division or growth arrest was observed in the controls that were treated with the vehicle alone.

EXAMPLE 3

Anti-tumoral Activity in Vivo

To evaluate the antitumoral activity of the combination of the invention a solid tumor strain LNCaP (ATCC) was used.

The cells were cultured for five to six times in nude mice. A solid cancer fragment of this strain (3 mm square) was transplanted beneath the skin of the axillary region of nu-nu nude male 8 week old mice (NxGen Biosciences, San Diego, Calif.). The mice in which the tumor was reliably taken (after about 20 days) were randomly assigned to 4 groups of 10 animals each. The animal groups were treated with vehicle, green tea extract, pomegranate or combination of green tea and pomegranate. The animals in control group received only drinking water whereas the green tea and pomegranate extract or their combination were administered at 1% in the drinking water (w/v, ad libitum) once a day in the morning for 28 consecutive days. Tumor diameter was measured twice a week, and tumor volume was calculated using formula 0.5238L1L2H where L1 is the long diameter, L2 the short diameter and H the height of the tumor. All animals were euthanized once the tumors reached around 1,300 mm3 in the control animals, which was after about 28 days.

The results (mean and SE) showed that the tumor volumes at day 28 were 1305±87 in the control group, whereas in the green tea and pomegranate extract treated groups the values were 1026±98 ($p<0.05$) and 1011±91 ($p<0.05$), respectively. Whereas in the combination treatment (green tea plus pomegranate extract) there was a definite synergistic effect on tumor reduction, 623±112 ($p<0.001$). Thus the inhibition was 52.3% by the combination compared to green tea (21.4%) or pomegranate (22.5%) alone.

The results obtained, reported in Table 15, show that the composition of the invention is statistically more active respect to the single constituents.

TABLE 15

| | CONTROL | (A) GREEN TEA | (B) POMEGRANATE | (A + B) GREEN TEA + POMEGRANATE |
|---|---|---|---|---|
| Tumor Volume mm³ ± SE | 1305 ± 87 | 1026 ± 98 | 1011 ± 91 | 623 ± 112 |
| P < vs control | | 0.05 | 0.05 | 0.001 |
| P < vs A | | | | 0.05 |
| P < vs B | | | | 0.05 |
| % inhibition vs control | | 21.4% | 22.5% | 52.3% |

The dietary supplement or medicament according to the present invention is composed of active ingredients which are familiar to operators in the medical field and already in use in clinical practice, and their pharmacotoxicological profiles are known.

Their procurement therefore is very easy, inasmuch as these are products which have been on the market now for a long time and are of a grade suitable for human or animal administration.

In the following are reported non limiting examples of compositions according to the present invention.

Composition 1
Green tea extract 250 mg;
pomegranate extract 250 mg.
Composition 2
Green tea extract 250 mg;
pomegranate extract 250 mg;
lycopene 1.25 mg;
selenium 82.5 μg,
zinc 20 mg.
Composition 3
Green tea extract 125 mg;
pomegranate extract 125 mg;
lycopene 5 mg;
selenium 82.5 μg,
zinc 20 mg;
serenoa 160 mg;
soya isoflavon 100 mg.
Composition 4
Green tea extract 125 mg;
pomegranate extract 40 mg;
lycopene 5 mg;
selenium 55 μg;

zinc 20 mg;
serenoa 320 mg;
soya isoflavon 100 mg.
Composition 5
Green tea extract 125 mg;
pomegranate extract 125 mg;
lycopene 5 mg;
selenium 82.5 µg,
zinc 20 mg;
serenoa 160 mg;
soya isoflavon 100 mg;
L-carnitine 200 mg.

The invention claimed is:

1. A composition for inhibiting or reducing the progression of prostate cancer in a patient consisting essentially of, as active ingredients, green tea extract in an amount of from 25 to 800 mg, pomegranate extract in an amount of from 25 to 800 mg, lycopene in an amount of from 0.03 to 30.0 mg, selenium in an amount of from 8.2 to 500 µg, zinc in an amount of from 1 to 200 mg, Serenoa repens extract in an amount of from 10 to 400 mg, soya isoflavonoids in an amount of from 10 to 500 mg, and L-carnitine in an amount of from 50 to 500 mg.

2. The composition of claim 1, wherein the green tea extract is present in an amount of 250 mg; the pomegranate extract is present in an amount of 250 mg; the lycopene is present in an amount of 1.25 mg; the selenium is present in an amount of 82.5 µg; and the zinc is present in an amount of 20 mg.

3. The composition of claim 1, wherein the green tea extract is present in an amount of 125 mg; the pomegranate extract is present in an amount of 125 mg; the lycopene is present in an amount of 5 mg; the selenium is present in an amount of 82.5 µg; the zinc is present in an amount of 20 mg; the Serenoa repens extract is present in an amount of 160 mg; and the soya isoflavonoids are present in an amount of 100 mg.

4. The composition of claim 1, wherein the green tea extract is present in an amount of 125 mg; the pomegranate extract is present in an amount of 40 mg; the lycopene is present in an amount of 5 mg; the selenium is present in an amount of 55 µg; the zinc is present in an amount of 20 mg; the Serenoa repens extract is present in an amount of 320 mg; and the soya isoflavonoids are present in an amount of 100 mg.

5. The composition of claim 1, wherein the green tea extract is present in an amount of 125 mg; the pomegranate extract is present in an amount of 125 mg; the lycopene is present in an amount of 5 mg; the selenium is present in an amount of 82.5 µg; the zinc is present in an amount of 20 mg; the Serenoa repens extract is present in an amount of 160 mg; the soya isoflavonoids are present in an amount of 100 mg; and the L-carnitine is present in an amount of 200 mg.

6. A method for inhibiting or reducing the progression of prostate cancer, comprising administering an effective amount of the composition of claim 1 to a patient in need thereof.

7. The method according to claim 6, further comprising administering co-enzymes, mineral substances, antioxidants, vitamins and agents useful for treating prostate cancer to the patient.

* * * * *